United States Patent
Kim et al.

(10) Patent No.: US 11,254,624 B2
(45) Date of Patent: Feb. 22, 2022

(54) METHOD AND APPARATUS FOR PREPARING ALPHA OLEFIN

(71) Applicant: LG CHEM, LTD., Seoul (KR)

(72) Inventors: Hye Bin Kim, Daejeon (KR); Eun Kyo Kim, Daejeon (KR); Mi Kyung Kim, Daejeon (KR); Joon Ho Shin, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 17/281,081

(22) PCT Filed: Aug. 4, 2020

(86) PCT No.: PCT/KR2020/010255
§ 371 (c)(1),
(2) Date: Mar. 29, 2021

(87) PCT Pub. No.: WO2021/033957
PCT Pub. Date: Feb. 25, 2021

(65) Prior Publication Data
US 2021/0340079 A1    Nov. 4, 2021

(30) Foreign Application Priority Data

Aug. 21, 2019  (KR) .................. 10-2019-0102507
Jul. 27, 2020  (KR) .................. 10-2020-0092937

(51) Int. Cl.
C07C 2/06    (2006.01)
B01J 19/18   (2006.01)
C07C 7/04    (2006.01)

(52) U.S. Cl.
CPC ............. *C07C 2/06* (2013.01); *B01J 19/1862* (2013.01); *B01J 2219/0004* (2013.01); *C07C 7/04* (2013.01)

(58) Field of Classification Search
CPC .......... C07C 2/06; C07C 7/04; B01J 19/1862; B01J 2219/0004; Y02P 20/582
See application file for complete search history.

(56) References Cited

U.S. PATENT DOCUMENTS 6,534,691 B2   3/2003   Culver et al.
9,856,184 B2   1/2018   Stochniol et al.
(Continued)

FOREIGN PATENT DOCUMENTS

CN   1490291 A       4/2004
JP   2007-119383 A   5/2007
(Continued)

OTHER PUBLICATIONS

Arthur Abraham, et al., "Ethylene to Linear, Alpha Olefins (1-Hexene & 1-Octene)", University of Pennsylvania, Department of Chemical & Biomolecular Engineering, 2013, pp. 1-882.

*Primary Examiner* — Ali Z Fadhel
(74) *Attorney, Agent, or Firm* — Dentons US LLP

(57) ABSTRACT

A method and an apparatus for preparing an alpha-olefin. The method includes supplying a feed stream including a gaseous ethylene monomer to a monomer dissolution device to dissolve the feed stream in a solvent and form a liquid ethylene monomer, and supplying a feed stream including the liquid ethylene monomer as a discharge stream to a reactor, thereby removing heat of dissolution of the gaseous ethylene monomer outside of the reactor, and decreasing an amount of a refrigerant used in an alpha-olefin production process to improve economic feasibility.

12 Claims, 1 Drawing Sheet

(56) References Cited

U.S. PATENT DOCUMENTS

| | | | |
|---|---|---|---|
| 2013/0090508 A1 | 4/2013 | Wang et al. | |
| 2013/0102826 A1* | 4/2013 | Lattner | C07C 2/08 |
| | | | 585/510 |
| 2016/0207849 A1* | 7/2016 | Stochniol | C07C 2/10 |
| 2016/0257630 A1* | 9/2016 | Stochniol | C07C 11/08 |

FOREIGN PATENT DOCUMENTS

| | | |
|---|---|---|
| JP | 2009-120588 A | 6/2009 |
| JP | 2009120588 A | 6/2009 |
| JP | 4458766 B2 | 2/2010 |
| JP | 2014-500251 A | 1/2014 |
| KR | 10-2012-0123131 A | 11/2012 |
| KR | 10-2015-0043313 A | 4/2015 |
| KR | 10-2017-0028203 A | 3/2017 |
| KR | 10-1749542 B1 | 6/2017 |

\* cited by examiner

[FIG. 1]
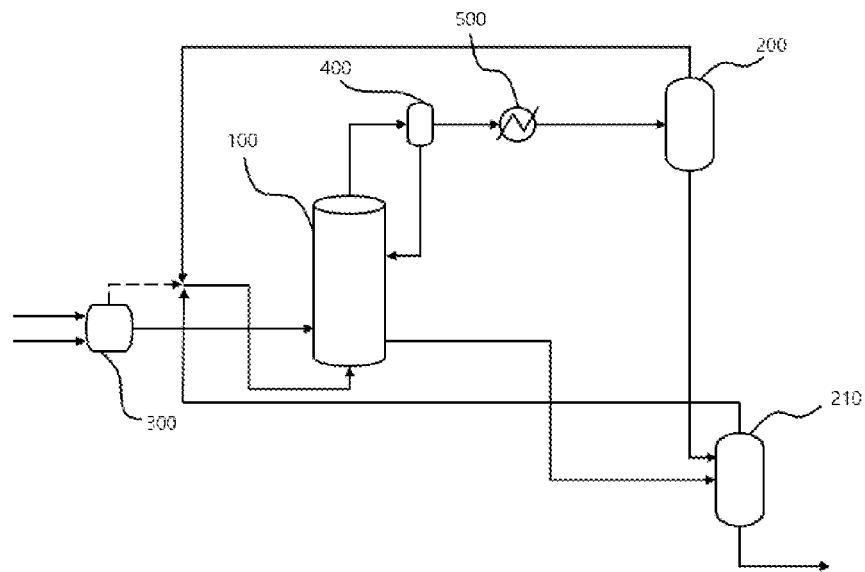
[FIG. 2]
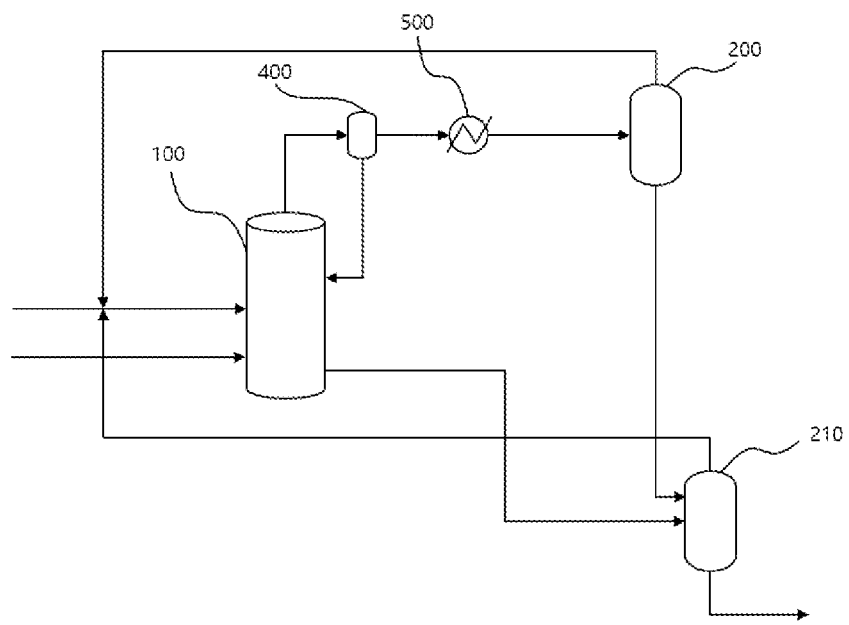

METHOD AND APPARATUS FOR PREPARING ALPHA OLEFIN

CROSS-REFERENCE TO RELATED APPLICATIONS

The present application is a National Stage Application of International Application No. PCT/KR2020/010255 filed on Aug. 4, 2020, which claims priority to and the benefit of priorities to Korean Patent Application No. 10-2019-0102507 filed on Aug. 21, 2019 and Korean Patent Application No. 10-2020-0092937 filed on Jul. 27, 2020, disclosures of which are incorporated by reference in their entirety for all purposes as if fully set forth herein.

FIELD OF DISCLOSURE

The present invention relates to a method for preparing an alpha-olefin and an apparatus for preparing an alpha-olefin, and more particularly, to a method for preparing an alpha-olefin and apparatus for preparing an alpha-olefin for decreasing a refrigerant use amount in an alpha-olefin production process for securing economic feasibility.

BACKGROUND

An alpha-olefin is an important material which is used in comonomers, cleaning agents, lubricants, plasticizers, and the like and is commercially widely used, and in particular, 1-hexene and 1-octene are often used as a comonomer for adjusting the density of polyethylene in the production of linear low-density polyethylene (LLDPE).

The alpha-olefin such as 1-hexene and 1-octene are produced representatively by an oligomerization reaction of ethylene. The ethylene oligomerization reaction is performed by an oligomerization reaction (trimerization reaction or tetramerization reaction) of ethylene using ethylene as a reactant, and since the product produced by the reaction includes by-products such as unreacted ethylene as well as a multi-component hydrocarbon mixture including 1-hexene and 1-octene to be desired, the product is subjected to a separation process by a distillation column, in which the unreacted ethylene is recovered and reused in the oligomerization reaction of ethylene.

When the ethylene monomer is oligomerized, significant heat of reaction is produced, and thus, removal of the heat of reaction is an important factor in designing a reactor. As a method of removing the heat of reaction, conventionally a method of supplying a monomer at a low temperature to remove the heat of reaction using sensible heat of the monomer has been used. However, the conventional heat removal method is a method in which an excessive amount of monomers supplied at a low temperature removes the heat of reaction while being heated up to a reaction temperature, and requires a large amount of a refrigerant for cooling the monomer to a low temperature, which is economically poor.

SUMMARY

Technical Problem

In order to solve the problems described in the Background Art, an object of the present invention is to provide a method for preparing an alpha-olefin and an apparatus for preparing an alpha-olefin which are economically improved by decreasing a use amount of a refrigerant used in the process.

That is, an object of the present invention is to provide a method and an apparatus for preparing an alpha-olefin and in which an ethylene monomer is supplied in a liquid phase to a reactor to remove heat of dissolution (latent heat) of the ethylene monomer outside of the reactor, thereby decreasing the amount of the refrigerant used in the process to improve economic feasibility.

Technical Solution

In one general aspect, a method for preparing an alpha-olefin includes: supplying a feed stream including a gaseous ethylene monomer to a monomer dissolution device to dissolve the feed stream in a solvent supplied to the monomer dissolution device and form a liquid ethylene monomer, and supplying a feed stream including the liquid ethylene monomer as a discharge stream from the monomer dissolution device to a reactor; oligomerizing the discharge stream from the monomer dissolution device which has been supplied to the reactor; supplying a part of a first discharge stream from the reactor to a first separation device and supplying a second discharge stream from the reactor to a second separation device; and recovering the ethylene monomer from each of the first separation device and the second separation device as an upper discharge stream, wherein in the monomer dissolution device, a dissolution rate of the gaseous ethylene monomer included in the feed stream in the solvent is 50% or more.

In another general aspect, an apparatus for preparing an alpha-olefin includes a monomer dissolution device for supplying a feed stream including a liquid ethylene monomer to a reactor, the liquid ethylene monomer being formed by dissolving a feed stream including a supplied gaseous ethylene monomer in a separately supplied solvent; a reactor for oligomerizing a supplied discharge stream from the monomer dissolution device, supplying a part of a first discharge stream to a first separation device, and supplying a second discharge stream to a second separation device; a first separation device which is supplied with the part of the first discharge stream from the reactor to recover the ethylene monomer as an upper discharge stream; and a second separation device which is supplied with the second discharge stream from the reactor to recover the ethylene monomer as an upper discharge stream, wherein in the monomer dissolution device, a dissolution rate of the gaseous ethylene monomer included in the feed stream in the solvent is 50% or more.

Advantageous Effects

According to the method for preparing an alpha-olefin and an apparatus for preparing an alpha-olefin of the present invention, a feed stream including a gaseous ethylene monomer is dissolved in a solvent and supplied as a liquid phase to a reactor, thereby removing heat of dissolution of the ethylene monomer outside the reactor, which causes a decrease in a refrigerant amount used in the process to secure economic feasibility.

In addition, a stream including the gaseous ethylene monomer is supplied from a naphtha cracking center, while maintaining a pressure of 20 bar to 80 bar which is the pressure of the supplier, thereby operating a monomer dissolution device at a higher pressure than the pressure of the reactor and improving a dissolution rate of the gaseous ethylene monomer dissolved in a solvent.

DESCRIPTION OF DRAWINGS

FIG. 1 is a process flowchart of a method for preparing an alpha-olefin according to an exemplary embodiment of the present invention.

FIG. 2 is a process flowchart of a method for preparing an alpha-olefin according to Comparative Example.

DETAILED DESCRIPTION

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

In the present invention, the term "stream" may refer to a fluid flow in a process, or may refer to a fluid itself flowing in a pipe. Specifically, the "stream" may refer to both a fluid itself flowing in a pipe connecting each apparatus and a fluid flow. In addition, the fluid may refer to a gas or a liquid.

Hereinafter, the present invention will be described in more detail for better understanding the present invention.

According to the present invention, a method for preparing an alpha-olefin is provided. As the method for preparing an alpha-olefin, a method for preparing an alpha-olefin including: supplying a feed stream including a gaseous ethylene monomer to a monomer dissolution device to dissolve the feed stream in a solvent supplied to the monomer dissolution device and form a liquid ethylene monomer, and supplying a feed stream including the liquid ethylene monomer as a discharge stream from the monomer dissolution device to a reactor; oligomerizing the discharge stream from the monomer dissolution device which has been supplied to the reactor; supplying a part of a first discharge stream from the reactor to a first separation device and supplying a second discharge stream from the reactor to a second separation device; and recovering the ethylene monomer from each of the first separation device and the second separation device as an upper discharge stream, wherein in the monomer dissolution device, a dissolution rate of the ethylene monomer included in the feed stream in the solvent is 50% or more, may be provided.

According to an exemplary embodiment of the present invention, a step of supplying the feed stream including the gaseous ethylene monomer to the monomer dissolution device to dissolve the feed stream in the solvent supplied to the monomer dissolution device and form a liquid ethylene monomer, and supplying a feed stream including the liquid ethylene monomer as a discharge stream from the monomer dissolution device to the reactor may be performed in a manner that the feed stream including the gaseous ethylene monomer is supplied to the monomer dissolution device, and the solvent separately supplied to the monomer dissolution device is used to dissolve the feed stream including the gaseous ethylene monomer, thereby supplying the feed stream including a liquid ethylene monomer to the reactor.

According to an exemplary embodiment of the present invention, the feed stream including the liquid ethylene monomer is supplied to the reactor as the discharge stream from the monomer dissolution device, and in the reactor, the supplied discharge stream from the monomer dissolution device is oligomerized to produce an alpha-olefin product to be desired. Here, the oligomerization reaction is performed in a lower part of the reactor, and the oligomerization reaction of the monomer may be performed in a liquid phase. The oligomerization reaction may refer to a reaction in which a monomer is oligomerized. The oligomerization may be referred to as trimerization or tetramerization depending on the number of monomers to be polymerized, and these are collectively called multimerization.

The alpha-olefin is an important material which is used in comonomers, cleaning agents, lubricants, plasticizers, and the like and is commercially widely used, and in particular, 1-hexene and 1-octene are often used as a comonomer for adjusting the density of polyethylene in the production of linear low-density polyethylene (LLDPE). The alpha-olefin such as 1-hexene and 1-octene may be produced by for example, a trimerization reaction or tetramerization reaction of ethylene.

According to an exemplary embodiment of the present invention, a step of oligomerizing a monomer may be performed in a reactor appropriate for a continuous process, and preferably performed under a reaction system including one or more reactors selected from the group consisting of a continuous stirred tank reactor (CSTR) and a plug flow reactor (PFR).

According to an exemplary embodiment of the present invention, the oligomerization reaction of a monomer may be performed by a homogeneous liquid phase reaction, a slurry reaction having a catalyst system in the form of being not dissolved partially or entirely, a two-phase liquid/liquid reaction, or a bulk phase reaction or gas phase reaction in which the product acts as a main medium, in the presence or absence of a solvent, by applying the reaction system and a common contact technology. Preferably, the step of oligomerizing a monomer may be performed in the homogeneous liquid phase reaction.

According to an exemplary embodiment of the present invention, the feed stream including the liquid ethylene monomer which is supplied to the reactor for performing the oligomerization reaction of the monomer is formed by dissolving a feed stream including a gaseous ethylene monomer supplied to the monomer dissolution device in a separately supplied solvent, as described above. As such, the feed stream including the gaseous ethylene monomer is dissolved in the solvent before being supplied to the reactor and supplied to the reactor as the feed stream including the liquid ethylene monomer. In such a process, heat of dissolution of the ethylene monomer is removed outside the reactor, thereby reducing the use amount of the refrigerant used in the alpha-olefin production process.

The feed stream including the gaseous ethylene monomer supplied to the monomer dissolution device may be supplied to the monomer dissolution device at a supply pressure of 20 bar to 80 bar. For example, the supply pressure of the feed stream including the gaseous ethylene monomer may be 20 bar to 58 bar, 25 bar to 55 bar, or 40 bar to 51 bar. The feed stream including the gaseous ethylene monomer is supplied to the monomer dissolution device at high pressure within the above range, thereby increasing the dissolution rate of the gaseous ethylene monomer dissolved in the solvent.

The supply pressure of the feed stream including the gaseous ethylene monomer may be higher than an operating pressure of the reactor. For example, the supply pressure of the feed stream including the gaseous ethylene monomer may be higher than the operating pressure of the reactor by 10 bar to 40 bar. As a specific example, the supply pressure of the feed stream including the gaseous ethylene monomer may be higher than the operating pressure of the reactor by 10 bar to 30 bar, 12 bar to 28 bar, or 15 bar to 25 bar. Thus, the monomer dissolution device may be operated at a higher pressure than a reactor operating pressure. For example, the operating pressure of the monomer dissolution device may be maintained at 20 bar to 80 bar, 30 bar to 60 bar, or 35 bar to 50 bar, due to the supply pressure of the feed stream including the gaseous ethylene monomer and the supply pressure of the solvent. As such, the monomer dissolution device is operated at a higher pressure than the reactor operating pressure, whereby the dissolution rate of the gaseous ethylene monomer dissolved in the solvent is increased, and when the discharge stream from the monomer dissolution device is supplied to the reactor, a separate device such as a pump for increasing even a reactor pressure may not be required.

A temperature of the discharge stream from the monomer dissolution device may be 30° C. to 50° C. For example, the temperature of the discharge stream from the monomer dissolution device may be 30° C. to 50° C., 35° C. to 50° C., or 35° C. to 45° C. In the method for preparing an alpha-olefin according to the present invention, the gaseous ethylene monomer is dissolved in the solvent in the monomer dissolution device and then supplied to the reactor, thereby dissolving the gaseous ethylene monomer at a high temperature such as 30° C. to 50° C., and here, the discharge stream from the monomer dissolution device may be partially cooled before being supplied to the reactor and a utility cost may be reduced by using cooling water instead of the refrigerant.

According to an exemplary embodiment of the present invention, the feed stream including the gaseous ethylene monomer supplied to the monomer dissolution device may be supplied from a naphtha cracking center (NCC). The naphtha cracking center may be carried out by including introducing each of naphtha, C2 and C3 hydrocarbon compounds, propane, and the like to a supply raw material and carrying out cracking in each pyrolysis furnace; cooling cracking gas which was pyrolyzed in each pyrolysis furnace to include hydrogen, and C1, C2, and C3 or higher hydrocarbon compounds; compressing the cooled cracking gas; and purifying a cracking compression stream including hydrogen, and C1, C2, and C3 or higher hydrocarbon compounds. Here, the feed stream including the gaseous ethylene monomer supplied to the monomer dissolution device may be a stream including ethylene (C2) which is separated from naphtha cracking.

A pressure of the stream including ethylene (C2) separated in the naphtha cracking center is 20 bar to 80 bar, and the stream is supplied to the monomer dissolution device as the feed stream including the gaseous ethylene monomer while maintaining the high pressure, thereby not requiring a separate device for transfer such as a pump and increasing the dissolution rate to be dissolved in the solvent.

In the monomer dissolution device, the dissolution rate of the ethylene monomer included in the feed stream in the solvent may be 50% or more, 55% to 100%, 70% to 100%, or 95% to 100%.

In the monomer dissolution device, the dissolution rate of the ethylene monomer included in the feed stream in the solvent may be measured by the following General Formula 1:

$$F2/F1 \times 100 \quad \text{[General Formula 1]}$$

wherein F1 is a flow rate (ton/hr) of the feed stream including the gaseous ethylene monomer, and F2 is a flow rate (ton/hr) of the ethylene monomer of a total flow rate of the discharge stream from the monomer dissolution device. Specifically, General Formula 1 may refer to the dissolution rate of the gaseous ethylene monomer dissolved in the solvent, in dissolving the feed stream including the gaseous ethylene monomer in the solvent in the monomer dissolution device to discharge the feed stream as the discharge stream from the monomer dissolution device. As such, 50% of the whole of the gaseous ethylene monomer is dissolved in the solvent and supplied to the reactor as the discharge stream from the monomer dissolution device, thereby effectively removing the heat of dissolution of the gaseous ethylene monomer outside the reactor to reduce the use amount of the refrigerant used in the process.

When in the monomer dissolution device, the dissolution rate of the ethylene monomer included in the feed stream in the solvent is not 100%, the gaseous ethylene monomer which is not dissolved in the solvent in the monomer dissolution device may be discharged as a separate stream and supplied to the reactor. Here, the gaseous ethylene monomer discharged from the monomer dissolution device may be supplied to the reactor as a separate stream, or may form a mixed stream with an upper discharge stream including the gaseous ethylene monomer which is recovered from each of a first separation device and a second separation device described later and supplied to the reactor in a mixer and then be supplied to the reactor as the mixed stream.

According to an exemplary embodiment of the present invention, the solvent supplied to the monomer dissolution device may be one or more selected from the group consisting of n-pentane, n-hexane, n-heptane, cyclohexane, methylcyclohexane, octane, cyclooctane, decane, dodecane, benzene, xylene, 1,3,5-trimethylbenzene, toluene, ethylbenzene, chlorobenzene, dichlorobenzene, and trichlorobenzene. As a specific example, the solvent may be methylcyclohexane.

The solvent supplied to the monomer dissolution device may be used in combination of two or more, if necessary. As a specific example, the solvent may be a mixture of methylcyclohexane and decane. When two or more solvents are used in combination as the solvent of methylcyclohexane mixed with decane having a high boiling point is used for dissolving the gaseous ethylene monomer, thereby liquefying the gaseous ethylene monomer at a higher temperature and improving the dissolution rate of the gaseous ethylene monomer in the solvent.

The temperature of the solvent supplied to the monomer dissolution device may be in a range of 10° C. to 50° C., and the pressure thereof may be 20 bar to 80 bar. For example, the supply temperature of the solvent may be in a range of 10° C. to 50° C., 20° C. to 50° C., or 35° C. to 45° C., and the supply pressure thereof may be 20 bar to 60 bar, 30 bar to 60 bar, or 35 bar to 50 bar. The solvent is supplied to the monomer dissolution device at the temperature and the pressure in the range described above, thereby liquefying the gaseous ethylene monomer at a relatively high temperature in the monomer dissolution device.

A flow rate of the solvent stream supplied to the monomer dissolution device may be in a range of 1 to 10 times, 2 to 6 times, or 2 to 4 times the content of the feed stream including the gaseous ethylene supplied to the monomer dissolution device. The solvent stream having the content in the range described above is supplied, thereby efficiently producing an oligomer product with a similar amount of the solvent to the amount of the solvent which has been used in the conventional method for preparing an alpha-olefin.

According to an exemplary embodiment of the present invention, the step of oligomerizing the discharge stream from the monomer dissolution device supplied to the reactor may be performed at a temperature of 10° C. to 180° C., 30° C. to 150° C., or 50° C. to 120° C. In addition, the step of oligomerizing may be performed under a pressure of 10 bar to 70 bar. For example, the step of oligomerizing may be performed under a pressure of 10 bar to 65 bar, 20 bar to 50 bar, or 25 bar to 35 bar. When ethylene is oligomerized within the temperature range and the pressure range, a selectivity to a desired alpha-olefin may be excellent, a by-product amount may be decreased, the operational efficiency of a continuous process may be increased, and the costs may be reduced.

According to an exemplary embodiment, in the step of supplying a first discharge stream from the reactor to a first separation device and supplying a second discharge stream from the reactor to a second separation device, a common flash drum, a condenser, a distillation column, and the like may be used as the separation device.

The first discharge stream from the reactor may be a stream including the gaseous ethylene monomer. The first discharge stream including the gaseous ethylene monomer may be supplied to a condenser and condensed in the condenser, the stream condensed into a liquid phase may be supplied from the condenser to the reactor, and the remaining stream except the stream condensed into the liquid phase in the condenser may be supplied to the first separation device via a heat exchanger. Then, the first separation device may supply the upper discharge stream including the gaseous ethylene monomer to the reactor and supply the lower discharge stream including the liquid ethylene monomer to the second separation device.

The first discharge stream from the reactor including the gaseous ethylene monomer is supplied to the first separation device, and cooling should be performed for efficiently recovering an unreacted ethylene monomer. To this end, the heat exchanger is provided in the present invention, and the gaseous ethylene monomer is cooled using a refrigerant in the heat exchanger. Here, in the present invention, the feed stream is supplied to the monomer dissolution device to dissolve the gaseous ethylene monomer in the solvent and supplies the monomer to the reactor as a liquid phase, thereby removing the heat of dissolution of the ethylene monomer outside the reactor, whereby a heat removal amount to be required in the heat exchanger is low to reduce a refrigerant use amount.

The second discharge stream from the reactor may be a stream including the liquid ethylene monomer. The second discharge stream including the liquid ethylene monomer is supplied to the second separation device with a lower discharge stream from the first separation device, and in the second separation device, an upper discharge stream including the gaseous ethylene monomer and a lower discharge stream including an alpha-olefin product, a by-product, and a solvent may be separated. The gaseous ethylene monomer recovered in the second separation device as the upper discharge stream may be supplied to the reactor.

The upper discharge stream including the gaseous ethylene monomer recovered from each of the first separation device and the second separation device may be supplied to the reactor. Here, the upper discharge stream from the first separation device and the upper discharge stream from the second separation device including the gaseous ethylene monomer may be supplied to the reactor via each stream, or may form a mixed stream using a mixer and be supplied to the reactor as the mixed stream.

According to an exemplary embodiment of the present invention, in the lower stream from the second separation device, the alpha-olefin product, the by-product, and the solvent may be separated by an additional separation process. The separated solvent may be supplied to the monomer dissolution device and reused. In addition, the separated alpha-olefin product may be separated again into a trimer, a tetramer, and the like of the ethylene monomer by an additional separation process.

According to the present invention, an apparatus for preparing an alpha-olefin is provided. As the apparatus for preparing an alpha-olefin, an apparatus for preparing an alpha-olefin including: a monomer dissolution device for supplying a feed stream including a liquid ethylene monomer to a reactor, the liquid ethylene monomer being formed by dissolving a feed stream including a supplied gaseous ethylene monomer in a separately supplied solvent; a reactor for oligomerizing the supplied discharge stream from the monomer dissolution device, supplying a part of a first discharge stream to a first separation device, and supplying a second discharge stream to a second separation device; a first separation device which is supplied with the part of the first discharge stream from the reactor to recover the ethylene monomer as an upper discharge stream; and a second separation device which is supplied with the second discharge stream from the reactor to recover the ethylene monomer as an upper discharge stream, may be provided.

According to an exemplary embodiment of the present invention, the apparatus for preparing an alpha-olefin according to the present invention may be an apparatus for performing the process according to the method for preparing an alpha-olefin described above.

According to an exemplary embodiment of the present invention, the apparatus for preparing an alpha-olefin according to the present invention may be described with reference to the following FIG. 1. For example, in the apparatus for preparing an alpha-olefin, a feed stream including a gaseous ethylene monomer is supplied to a monomer dissolution device 300 and dissolved in a solvent separately supplied to the monomer dissolution device 300, thereby supplying a feed stream including a liquid ethylene monomer to a reactor 100 as a discharge stream from the monomer dissolution device 300. Here, a separate pump (not shown) may be used in the solvent supplied to the monomer dissolution device 300, for increasing a pressure of the monomer dissolution device 300.

In the monomer dissolution device 300, the dissolution rate of the gaseous ethylene monomer included in the feed stream in the solvent may be controlled to 50% or more, 55% to 100%, 70% to 100%, or 95% to 100%. In the monomer dissolution device 300, the dissolution rate of the gaseous ethylene monomer included in the feed stream is controlled within the range, thereby removing heat of dissolution of the ethylene monomer outside the reactor, whereby a heat removal amount to be required in the heat exchanger is low to reduce a refrigerant use amount.

The discharge stream from the monomer dissolution device 300 is supplied to the reactor 100 to be oligomerized in the reactor 100, and when the dissolution rate of the gaseous ethylene monomer included in the feed stream is not 100% in the monomer dissolution device 300, the gaseous ethylene monomer which is not dissolved may be supplied to the reactor 100 as a separate stream.

In the reactor 100, the first discharge stream including the gaseous ethylene monomer and the second discharge stream including the liquid ethylene monomer may be separated. The thus-separated first discharge stream including the gaseous ethylene monomer is supplied to a first separation device 200, and the second discharge stream including the liquid ethylene monomer may be supplied to a second separation device 210.

The stream including the ethylene monomer supplied to the reactor 100 may further include a stream including the ethylene monomer recovered from the upper discharge stream from the first separation device 200 and the second separation device 210, together with the discharge stream from the monomer dissolution device 300. Here, the upper discharge stream from the first separation device 200 and the upper discharge stream from the second separation device 210 may be supplied to the reactor 100 as a separate stream, or supplied to the reactor 100 as a mixed discharge stream which is mixed in a mixer (not shown).

The first discharge stream from the reactor 100 is supplied to a condenser 400, a stream including a condensed liquid monomer is resupplied to the reactor 100, and a stream except the stream resupplied to the reactor 100 of the first discharge stream from the reactor 100 is supplied to the first separation device 200 partially at a lower temperature using a refrigerant in a heat exchanger 500 via the heat exchanger 500.

According to an exemplary embodiment of the present invention, the first separation device 200 may be supplied with the first discharge stream from the reactor 100 and separated into an upper discharge stream including the gaseous ethylene monomer and a lower discharge stream including the liquid ethylene monomer. Here, the upper discharge stream from the first separation device 200 may be supplied to the reactor 100, and the lower discharge stream may be supplied to the second separation device 210.

According to an exemplary embodiment of the present invention, the second separation device 210 may be supplied with the second discharge stream from the reactor 100 and the lower discharge stream from the first separation device 200 including the liquid monomer, and may be separated into the upper discharge stream including the gaseous ethylene monomer and the lower discharge stream including the alpha-olefin product, the by-product, and the solvent. Here, the upper discharge stream from the second separation device 210 may be supplied to the reactor 100, and the lower discharge stream including the alpha-olefin product and the solvent may be recovered.

Here, the alpha-olefin product and the solvent included in the lower discharge stream from a second separation device 210 may be separated by an additional separation device (not shown), and the separated solvent may be reused in an alpha-olefin production process. Here, the alpha-olefin product may include 1-hexene and 1-octene. In this case, 1-hexene and 1-octene may be separated by an additional separation device (not shown) or separated by a separate process and used.

According to an exemplary embodiment of the present invention, the apparatus for preparing an alpha-olefin may further selectively include a stream supplied to the reactor 100, the first separation device 200, the second separation device 210, and the monomer dissolution device 300, if necessary, in addition to the configurations described above.

According to an exemplary embodiment of the present invention, in the apparatus for preparing an alpha-olefin, a condenser (not shown), a reboiler (not shown), a pump (not shown), a compressor (not shown), a mixer (not shown), and the like may be further installed, if necessary.

Hereinabove, the method for preparing an apparatus for preparing an alpha-olefin according to the present invention have been described and illustrated in the drawings, but the description and the illustration in the drawings are those of only core configurations for understanding of the present invention, and in addition to the process and apparatus described above and illustrated in the drawings, the process and the apparatus which are not described and illustrated separately may be appropriately applied and used for carrying out the method for preparing an alpha-olefin and apparatus for preparing an alpha-olefin according to the present invention.

Hereinafter, the present invention will be described in more detail by the Examples. However, the following Examples are provided for illustrating the present invention. It is apparent to a person skilled in the art that various modifications and alterations may be made without departing from the scope and spirit of the present invention, and the scope of the present invention is not limited thereto.

EXAMPLES

Example 1

For the process flowchart illustrated in FIG. 1, the process was simulated using an Aspen Plus simulator from Aspen Technology, Inc. Here, a gaseous ethylene monomer C2 as a feed stream was supplied to a monomer dissolution device 300 at a flow rate of 13 ton/hr while maintaining a pressure of 50 bar which is the pressure of the supplier, and methylcyclohexane as a solvent was supplied at a flow rate of 39 ton/hr with the pressure of 50 bar increased using a pump. Here, a supply amount of the solvent introduced was three times a supply amount of a gaseous ethylene monomer. In addition, an operating temperature of the reactor 100 was set at 80° C., and an operating pressure was set at 15 bar. The results are shown in the following Table 1.

TABLE 1

| | Stream 1 | Stream 2 | Stream 3 | Stream 4 | Stream 5 | Stream 6 |
|---|---|---|---|---|---|---|
| Phase | Gaseous | Liquid | Liquid | Gaseous | Gaseous | Gaseous/liquid |
| Temperature (° C.) | 30 | 39 | 40 | 80 | 40 | 20 |
| Pressure (bar) | 50 | 50 | 50 | 15 | 15 | 15 |
| Flow rate (ton/hr) | 13 | 39 | 52 | 208 | 182 | 182 |
| Ethylene (ton/hr) | 13 | 0 | 13 | 164 | 162 | 162 |
| Solvent (ton/hr) | 0 | 39 | 39 | 22 | 5 | 5 |

Stream 1: a feed stream supplied to the monomer dissolution device 300
Stream 2: a solvent stream supplied to the monomer dissolution device 300
Stream 3: a discharge stream from the monomer dissolution device 300
Stream 4: an upper discharge stream from the reactor 100 supplied to the condenser 400
Stream 5: a stream supplied from the condenser 400 to the heat exchanger 500
Stream 6: a stream supplied from the heat exchanger 500 to the first separation device 200

Referring to Table 1, it was found that the ethylene monomer was supplied to the monomer dissolution device 300 at a flow rate of 13 ton/hr, a temperature of 30° C., and a pressure of 50 bar, the solvent was supplied at a flow rate of 39 ton/hr, a temperature of 39° C., and a pressure of 50 bar, so that the gaseous ethylene monomer was dissolved in the solvent. Here, the operating pressure of the monomer dissolution device 300 was confirmed to be 50 bar due to the supply pressure of the ethylene monomer.

The gaseous ethylene monomer was dissolved in the solvent, and the stream including the liquid ethylene monomer was supplied to the reactor 100 as the discharge stream from the monomer dissolution device 300. Here, it was found that the discharge stream from the monomer dissolution device 300 was liquid, the temperature thereof was 40° C., and the ethylene monomer (stream 1) was dissolved in the solvent (stream 2) at a dissolution rate of 100%.

The stream including the monomer supplied to the reactor 100 includes the upper discharge stream from the first separation device 200 and the second separation device 210, in addition to the discharge stream from the monomer dissolution device 300. The stream including the ethylene monomer recovered as the upper discharge stream from the first separation device 200 had a temperature of 23° C., a pressure of 15 bar, and a flow rate of 177 ton/hr, and the stream including the monomer recovered as the upper discharge stream from the second separation device 210 had a temperature of 0° C., a pressure of 15 bar, and a flow rate of 2 ton/hr.

Here, the upper discharge stream from the reactor 100 was condensed in the condenser 400, and a portion thereof was resupplied to the reactor 100 and the remainder was supplied to the first separation device 200 via the heat exchanger 500, and it was confirmed that the refrigerant amount used in the heat exchanger 500 was 1,880 Mcal/hr.

Example 2

The process was performed in the same manner as in Example 1, except that the temperature of the feed stream supplied to the monomer dissolution device 300 was controlled to 30° C. and the pressure thereof was controlled to 50 bar, and the temperature of the solvent stream was controlled to 37° C. and the pressure thereof was controlled to 40 bar. The results are shown in the following Table 2.

TABLE 2

| | Stream 1 | Stream 2 | Stream 3 | Stream 4 | Stream 5 | Stream 6 |
|---|---|---|---|---|---|---|
| Phase | Gaseous | Liquid | Liquid | Gaseous | Gaseous | Gaseous/liquid |
| Temperature (° C.) | 30 | 37 | 40 | 80 | 40 | 17 |
| Pressure (bar) | 50 | 40 | 40 | 15 | 15 | 15 |
| Flow rate (ton/hr) | 13 | 39 | 47 | 208 | 182 | 182 |
| Ethylene (ton/hr) | 13 | 0 | 9 | 164 | 162 | 162 |
| Solvent (ton/hr) | 0 | 39 | 39 | 22 | 5 | 5 |

Stream 1: a feed stream supplied to the monomer dissolution device 300
Stream 2: a solvent stream supplied to the monomer dissolution device 300
Stream 3: a discharge stream from the monomer dissolution device 300
Stream 4: an upper discharge stream from the reactor 100 supplied to the condenser 400
Stream 5: a stream supplied from the condenser 400 to the heat exchanger 500
Stream 6: a stream supplied from the heat exchanger 500 to the first separation device 200

Referring to Table 2, in Example 2, the operating pressure of the monomer dissolution device 300 was controlled to 40 bar to dissolve the gaseous ethylene monomer at a dissolution rate of about 67%, and the gaseous ethylene monomer which was not dissolved was discharged from the monomer dissolution device 300 as a separate stream to be supplied to the reactor 100, as compared with Example 1.

As such, it was confirmed that the gaseous ethylene monomer in the feed stream was dissolved at the level described above, whereby the refrigerant for removing heat of dissolution in the process was somewhat increased as compared with Example 1, and the refrigerant amount used in the heat exchanger 500 was 2,148 Mcal/hr, which was somewhat increased as compared with Example 1.

Example 3

The process was performed in the same manner as in Example 1, except that the temperature of the feed stream supplied to the monomer dissolution device 300 was controlled to 30° C. and the pressure thereof was controlled to 50 bar, and the temperature of the solvent stream was controlled to 36° C. and the pressure thereof was controlled to 35 bar. The results are shown in the following Table 3.

TABLE 3

| | Stream 1 | Stream 2 | Stream 3 | Stream 4 | Stream 5 | Stream 6 |
|---|---|---|---|---|---|---|
| Phase | Gaseous | Liquid | Liquid | Gaseous | Gaseous | Gaseous/liquid |
| Temperature (° C.) | 30 | 36 | 40 | 80 | 40 | 15 |
| Pressure (bar) | 50 | 35 | 35 | 15 | 15 | 15 |
| Flow rate (ton/hr) | 13 | 39 | 45 | 208 | 182 | 182 |
| Ethylene (ton/hr) | 13 | 0 | 7 | 164 | 162 | 162 |
| Solvent (ton/hr) | 0 | 39 | 38 | 22 | 5 | 5 |

Stream 1: a feed stream supplied to the monomer dissolution device 300
Stream 2: a solvent stream supplied to the monomer dissolution device 300
Stream 3: a discharge stream from the monomer dissolution device 300
Stream 4: an upper discharge stream from the reactor 100 supplied to the condenser 400
Stream 5: a stream supplied from the condenser 400 to the heat exchanger 500
Stream 6: a stream supplied from the heat exchanger 500 to the first separation device 200

Referring to Table 3, in Example 3, the operating pressure of the monomer dissolution device 300 was controlled to 35 bar to dissolve the gaseous ethylene monomer at a dissolution rate of about 54%, and the gaseous ethylene monomer which was not dissolved was discharged from the monomer dissolution device 300 as a separate stream to be supplied to the reactor 100, as compared with Example 1.

As such, it was confirmed that the gaseous ethylene monomer in the feed stream was dissolved at the level described above, whereby the refrigerant for removing heat of dissolution in the process was somewhat increased as compared with Example 1, and the refrigerant amount used in the heat exchanger 500 was 2,278 Mcal/hr, which was somewhat increased as compared with Examples 1 and 2.

COMPARATIVE EXAMPLES

Comparative Example 1

For the process flowchart illustrated in FIG. 2, the process was simulated using an Aspen Plus simulator from Aspen Technology, Inc. Here, the gaseous ethylene monomer C2 supplied to the reactor 100 as the feed stream was supplied at a flow rate of 13 ton/hr while maintaining the pressure of 50 bar which was the pressure of the supplier, and mixed with the ethylene monomer recovered in the process in a mixer (not shown) and supplied to the reactor 100. In addition, as the solvent separately supplied to the reactor 100, methylcyclohexane was used and supplied at a flow rate of 39 ton/hr/Here, a supply amount of the solvent was introduced three times a supply amount of a gaseous ethylene monomer. In addition, the operating temperature of the reactor 100 was set to 80° C. and the operating pressure thereof was set to 15 bar, and the total flow rate of the ethylene monomer introduced for the oligomerization reaction and removal of heat of reaction was maintained the same as Example 1. The results are shown in the following Table 4.

TABLE 4

|  | Stream 1-1 | Stream 2-1 | Stream 3-1 | Stream 4-1 | Stream 5-1 |
|---|---|---|---|---|---|
| Phase | Gaseous | Liquid | Gaseous | Gaseous | Gaseous/liquid |
| Temperature (° C.) | 30 | 33 | 80 | 40 | 15 |
| Pressure (bar) | 50 | 15 | 15 | 15 | 15 |
| Flow rate (ton/hr) | 13 | 39 | 207 | 182 | 182 |
| Ethylene (ton/hr) | 13 | 0 | 163 | 162 | 162 |
| Solvent (ton/hr) | 0 | 39 | 22 | 5 | 5 |

\* Stream 1-1: a feed stream supplied to the reactor 100
\* Stream 2-1: a solvent stream supplied to the Reactor 100
\* Stream 3-1: an upper discharge stream from the reactor 100 supplied to the condenser 400
\* Stream 4-1: a stream supplied from the condenser 400 to the heat exchanger 500
\* Stream 5-1: a stream supplied from the heat exchanger 500 to the first separation device 200

Referring to Table 4, in Comparative Example 1, the gaseous ethylene monomer in the feed stream was not dissolved in the solvent and supplied to the reactor 100, but the feed stream and the solvent stream were supplied to the reactor 100 as each stream, as compared with Examples.

The gaseous ethylene monomer was not dissolved outside the reactor 100 and supplied to the reactor 100, and dissolved in the solvent supplied to the reactor 100 with being mixed with the solvent, and the heat of dissolution occurred at this time. Thus, it was confirmed that a refrigerant for removing the heat of dissolution in the process was further required as compared with Example 1, and the refrigerant amount used in the heat exchanger 500 was 2,313 Mcal/hr, which was increased by about 23%, as compared with the refrigerant amount of 1,880 Mcal/hr, which was used in the heat exchanger 500 of Example 1.

Comparative Example 2

The process was performed in the same manner as in Example 1, except that the supply temperature of the solvent supplied to the monomer dissolution device 300 was controlled to 33° C. and the supply pressure thereof was supplied at 15 bar, and the operating pressure of the monomer dissolution device 300 was controlled to 15 bar so that the pressure became the same as the operating pressure of the reactor 100. The results are shown in the following Table 5.

TABLE 5

|  | Stream 1-2 | Stream 2-2 | Stream 3-2 | Stream 4-2 | Stream 5-2 | Stream 6-2 |
|---|---|---|---|---|---|---|
| Phase | Gaseous | Liquid | Liquid | Gaseous | Gaseous | Gaseous/liquid |
| Temperature (° C.) | 30 | 33 | 28 | 80 | 40 | 15 |
| Pressure (bar) | 50 | 15 | 15 | 15 | 15 | 15 |
| Flow rate (ton/hr) | 13 | 39 | 41 | 207 | 182 | 182 |
| Ethylene (ton/hr) | 13 | 0 | 3 | 163 | 162 | 162 |
| Solvent (ton/hr) | 0 | 39 | 38 | 22 | 5 | 5 |

Stream 1-2: a feed stream supplied to the monomer dissolution device 300
Stream 2-2: a solvent stream supplied to the monomer dissolution device 300
Stream 3-2: a discharge stream from the monomer dissolution device 300
Stream 4-2: an upper discharge stream from the reactor 100 supplied to the condenser 400
Stream 5-2: a stream supplied from the condenser 400 to the heat exchanger 500
Stream 6-2: a stream supplied from the heat exchanger 500 to the first separation device 200

Referring to Table 5, in Comparative Example 2, the gaseous ethylene monomer was dissolved in the solvent stream at a dissolution rate of about 23% in the monomer dissolution device 300, and the gaseous ethylene monomer which was not dissolved was discharged from the monomer dissolution device 300 as a separate stream to be supplied to the reactor 100, as compared with Example 1.

As such, the gaseous ethylene monomer in the feed stream was dissolved at the level described above, whereby the refrigerant for removing the heat of dissolution in the process was further required as compared with Example 1, and the refrigerant amount used in the heat exchanger 500 was 2,313 kcal/hr which is at the same level as Comparative Example 1, and thus, the effect of decreasing a refrigerant use amount as in Examples 1 to 3 was not shown.

The invention claimed is:

1. A method for preparing an alpha-olefin comprising:
   supplying a feed stream including a gaseous ethylene monomer to a monomer dissolution device to dissolve the feed stream in a solvent supplied to the monomer dissolution device and form a liquid ethylene monomer, and supplying a feed stream including the liquid ethylene monomer as a discharge stream from the monomer dissolution device to a reactor;
   oligomerizing the discharge stream from the monomer dissolution device which has been supplied to the reactor;
   supplying a part of a first discharge stream from the reactor to a first separation device and supplying a second discharge stream from the reactor to a second separation device; and
   recovering an unreacted ethylene monomer from each of the first separation device and the second separation device as an upper discharge stream,
   wherein in the monomer dissolution device, a dissolution rate of the gaseous ethylene monomer included in the feed stream in the solvent is 50% or more.

2. The method for preparing an alpha-olefin of claim 1, wherein in the monomer dissolution device, the dissolution rate of the gaseous ethylene monomer included in the feed stream in the solvent is 95% to 100%.

3. The method for preparing an alpha-olefin of claim 1, wherein a supply pressure of the feed stream including the gaseous ethylene monomer is 20 bar to 80 bar.

4. The method for preparing an alpha-olefin of claim 1, wherein a pressure of the solvent supplied to the monomer dissolution device is 20 bar to 80 bar.

5. The method for preparing an alpha-olefin of claim 1, wherein an operating pressure of the monomer dissolution device is higher than an operating pressure of the reactor.

6. The method for preparing an alpha-olefin of claim 1, wherein the operating pressure of the monomer dissolution device is 20 bar to 80 bar.

7. The method for preparing an alpha-olefin of claim 1, wherein a temperature of the discharge stream from the monomer dissolution device is 30° C. to 50° C.

8. The method for preparing an alpha-olefin of claim 1, wherein the feed stream including the gaseous ethylene monomer is supplied from a naphtha cracking center.

9. The method for preparing an alpha-olefin of claim 1, wherein the solvent is one or more selected from the group consisting of n-pentane, n-hexane, n-heptane, cyclohexane, methylcyclohexane, octane, cyclooctane, decane, dodecane, benzene, xylene, 1,3,5-trimethylbenzene, toluene, ethylbenzene, chlorobenzene, dichlorobenzene, and trichlorobenzene.

10. The method for preparing an alpha-olefin of claim 1, wherein the upper discharge stream including the ethylene monomer recovered from each of the first separation device and the second separation device is supplied to the reactor.

11. The method for preparing an alpha-olefin of claim 1, wherein the first discharge stream from the reactor is supplied to a condenser, a part of a discharge stream from the condenser is supplied to the reactor, and a remaining stream is supplied to the first separation device via a heat exchanger.

12. An apparatus for preparing an alpha-olefin, comprising:
- a monomer dissolution device for supplying a feed stream including a liquid ethylene monomer to a reactor, the liquid ethylene monomer being formed by dissolving a feed stream including a supplied gaseous ethylene monomer in a separately supplied solvent;
- a reactor for oligomerizing a supplied discharge stream from the monomer dissolution device, supplying a part of a first discharge stream to a first separation device, and supplying a second discharge stream to a second separation device;
- a first separation device which is supplied with the part of the first discharge stream from the reactor to recover an unreacted ethylene monomer as an upper discharge stream; and
- a second separation device which is supplied with the second discharge stream from the reactor to recover an unreacted ethylene monomer as an upper discharge stream,
- wherein in the monomer dissolution device, a dissolution rate of the gaseous ethylene monomer included in the feed stream in the solvent is controlled to be 50% or more.

* * * * *